(12) United States Patent
Ito

(10) Patent No.: US 9,527,681 B2
(45) Date of Patent: Dec. 27, 2016

(54) THIN-SECTION SAMPLE FABRICATION APPARATUS AND METHOD OF FABRICATING THIN-SECTION SAMPLE

(71) Applicant: SAKURA FINETEK JAPAN CO., LTD., Tokyo (JP)

(72) Inventor: Tetsumasa Ito, Kawasaki (JP)

(73) Assignee: SAKURA FINETEK JAPAN CO., LTD., Tokyo (JP)

( * ) Notice: Subject to any disclaimer, the term of this patent is extended or adjusted under 35 U.S.C. 154(b) by 131 days.

(21) Appl. No.: 14/376,725

(22) PCT Filed: Feb. 6, 2013

(86) PCT No.: PCT/JP2013/052687
§ 371 (c)(1),
(2) Date: Aug. 5, 2014

(87) PCT Pub. No.: WO2013/118753
PCT Pub. Date: Aug. 15, 2013

(65) Prior Publication Data
US 2015/0008096 A1     Jan. 8, 2015

(30) Foreign Application Priority Data

Feb. 8, 2012 (JP) ................................. 2012-025280

(51) Int. Cl.
*G01N 21/00* (2006.01)
*B65G 49/00* (2006.01)
(Continued)

(52) U.S. Cl.
CPC .............. *B65G 49/00* (2013.01); *B65G 15/00* (2013.01); *G01N 1/2813* (2013.01); *G02B 21/34* (2013.01);
(Continued)

(58) Field of Classification Search
CPC ........................................................ G01N 1/31
See application file for complete search history.

(56) References Cited

U.S. PATENT DOCUMENTS

2007/0039435 A1   2/2007  Kokubo
2008/0044260 A1*  2/2008  Miyatani ................. G01N 1/06
                                                         414/222.11

FOREIGN PATENT DOCUMENTS

EP    1 903 325    3/2008
JP    2002-022626  1/2002
(Continued)

OTHER PUBLICATIONS

Search Report from corresponding European Application No. 13746618.1 dated Aug. 28, 2015. English translation attached.
(Continued)

*Primary Examiner* — Jyoti Nagpaul
(74) *Attorney, Agent, or Firm* — Grossman, Tucker, Perreault & Pfleger, PLLC

(57) ABSTRACT

A thin-section sample fabrication apparatus includes a sample table that places a thin section cut out from an embedding block, a transporting mechanism that moves the thin section to the vicinity of the sample table, a liquid phase forming portion that forms a liquid phase having a predetermined amount of transfer liquid which continues from the transport surface onto the sample table, and a thin-section transfer portion that transfers the thin section onto the sample table so that a surface of the thin section opposing the transport surface opposes the sample table by surface tension of the liquid phase formed by the liquid phase forming portion.

3 Claims, 6 Drawing Sheets

(51) Int. Cl.
*G02B 21/34* (2006.01)
*B65G 15/00* (2006.01)
*G01N 1/28* (2006.01)
*G01N 1/06* (2006.01)
*G01N 35/04* (2006.01)
*G01N 1/31* (2006.01)

(52) U.S. Cl.
CPC ................ *G01N 1/06* (2013.01); *G01N 1/312* (2013.01); *G01N 35/04* (2013.01)

(56) References Cited

FOREIGN PATENT DOCUMENTS

| | | |
|---|---|---|
| JP | 2004-028910 | 1/2004 |
| JP | 3745556 | 2/2006 |
| JP | 2007-057255 | 3/2007 |
| JP | 2008-076249 | 4/2008 |
| JP | 2008-164521 | 7/2008 |
| JP | 2009-180546 | 8/2009 |

OTHER PUBLICATIONS

International Search Report from corresponding PCT Application No. PCT/JP2013/052687 dated Apr. 9, 2013. English translation attached.

\* cited by examiner

THIN-SECTION SAMPLE FABRICATION APPARATUS AND METHOD OF FABRICATING THIN-SECTION SAMPLE

TECHNICAL FIELD

The present invention relates to a thin-section sample fabrication apparatus and a method of fabricating the same.

Priority is claimed on Japanese Patent Application No. 2012-025280, filed Feb. 8, 2012, the content of which is incorporated herein by reference.

BACKGROUND ART

In pathological examinations of cells or the like, an observation object sample is sliced to perform a microscope observation of the sample.

In general, in order to slice soft tissues and cells so as not to break the tissues and forms of the cells, the sample is embedded in paraffin in advance, and an embedding block is fabricated. Next, the embedding block is thinly sliced (is thinly sectioned) to a thickness of 2 to 5 μm, and a thin section is fabricated. Accordingly, even when an observation object is soft tissues or the like, the soft tissues can be very thinly sliced without destroying the forms of the tissues. Moreover, the thin section is fixed onto a sample table such as a slide glass, and the thin-section sample is fabricated.

In a fabrication process of the thin-section sample, after the thin section is cut out from the embedding block by a cutting blade, the thin section is transported to a predetermined member, and it is necessary to place the thin section onto the sample table (for example, slide glass) in a state where wrinkles, slack, or the like does not exist.

A thin-section sample fabrication apparatus which automates the process and a method of fabricating the same are proposed (for example, refer to Patent Documents 1 and 2).

In a technique disclosed in Patent Document 1, a folded-back end of a belt which is a transporting mechanism is disposed to be inclined to a liquid surface in a liquid tank. A thin section, which is placed on the belt and is transported, is released into the liquid tank, the released thin section is pulled-up by a slide glass which is held to a pulling-up mechanism, and the thin section is placed onto the slide glass.

In a technique disclosed in Patent Document 2, a carrier tape, to which a thin section is adsorbed, moves to an upper portion of a slide glass so that the thin section is placed to a lower surface of the tape. Transfer water drops on an upper surface of the slide glass. When the thin section moves to the upper portion of the slide glass, the carrier tape is bent to the lower portion, and the thin section on the carrier tape is transferred onto the transfer water on the slide glass.

PRIOR ART DOCUMENTS

Patent Documents

[Patent Document 1] Japanese Unexamined Patent Application, First Publication No. 2009-180546
[Patent Document 2] Japanese Patent No. 3745556

DISCLOSURE OF INVENTION

Problems to be Solved by the Invention

In the technique disclosed in Patent Document 1, the folded-back end of the belt inclined to the liquid surface is disposed in the liquid tank, and the slide glass for pulling up the thin section in the liquid tank is submerged. Therefore, if a length (75 mm) of a standard slide glass is considered, the depth of the liquid tank needs be a minimum of 60 mm, and the size of the overall apparatus is increased.

In addition, in the case of the technique disclosed in Patent Document 1, a total flow rate of the liquid flowing in the liquid tank is increased, and a generation amount of bubbles is increased approximately in proportion with a volume of the liquid. Therefore, when the thin section is pulled up on the slide glass in the liquid tank, a possibility of entering of bubbles due to the thin section is increased.

On the other hand, in the technique disclosed in Patent Document 2, the absorption of the thin section with respect to the carrier tape and the receiving of the thin section to the slide glass are performed, using the surface tension of the liquid. Therefore, when the thin section adsorbed to the carrier tape simply contacts the transfer water on the slide glass, it is predicted that a possibility of the thin section being transferred from the carrier tape onto the slide glass is approximately 50%.

Therefore, in the technique disclosed in Patent Document 2, for the proportion of movements of the thin section from the carrier tape onto the slide glass to be increased, it is necessary to carry out complicated and specific operations to the carrier tape.

Accordingly, the present invention is to provide a thin-section sample fabrication apparatus and a method of fabricating a thin-section sample capable of easily and securely placing a thin section, which is adsorbed to and placed on a transport surface by surface tension of water, on a sample table using a small amount of transfer liquid.

Means for Solving the Problems

According to a first aspect of the present invention, there is provided a thin-section sample fabrication apparatus including: a sample table that places a thin section cut out from an embedding block in which a biological sample is embedded; a transporting mechanism that includes a transport surface on which the thin section is placed, and moves the thin section placed on the transport surface to the vicinity of the sample table; a liquid phase forming portion that forms a liquid phase having a predetermined amount of transfer liquid which continues from the transport surface onto the sample table, in the vicinity of the sample table; and a thin-section transfer portion that transfers the thin section placed on the transport surface onto the sample table so that a surface of the thin section placed on the transport surface opposing the transport surface opposes the sample table by surface tension of the liquid phase formed by the liquid phase forming portion.

In the thin-section sample fabrication apparatus, the liquid phase having a predetermined amount of transfer liquid which continues from the transport surface onto the sample table is formed by the liquid phase forming portion. If the thin section reaches the thin-section transfer portion in the state where the liquid phase is formed, the thin section receives a pushing force from the transport surface, moves from the transport surface onto the liquid phase of the transfer liquid, and is transferred onto the liquid phase. Therefore, it is possible to easily and securely place the thin section, which is adsorbed to and placed on the transport surface by the surface tension of water, onto the sample table using a small amount of transfer liquid.

According to a second aspect of the present invention, in the thin-section sample fabrication apparatus of the first aspect, the liquid phase forming portion may supply the transfer liquid to the transport surface, and may form the liquid phase having the predetermined amount of transfer liquid continuing from the transport surface onto the sample table.

Accordingly, the transfer liquid supplied to the transport surface forms the liquid phase, which continues from the transport surface onto the sample table, along the transport surface.

According to a third aspect of the present invention, the thin-section sample fabrication apparatus of the first or second aspect may further include a relative displacement mechanism that relatively displaces the sample table and the thin-section transfer portion in a transfer direction of the thin section onto the sample table when the thin section is transferred from the transport surface onto the sample table.

When the thin section is transferred from the transport surface onto the sample table, if the relative displacement mechanism relatively displaces the sample table and the thin-section transfer portion, a curved shape of the liquid phase in a transfer advancement direction formed between the transport surface and the sample table is extended. Accordingly, the thin section is smoothly transferred onto the sample table.

According to a fourth aspect of the present invention, the thin-section sample fabrication apparatus of the first or second aspect may further include a sample table inclination mechanism that inclines the sample table downward in a transfer direction of the thin section when the thin section is transferred from the transport surface onto the sample table.

When the thin section is transferred from the transport surface onto the sample table, if the sample table inclination mechanism inclines the sample table downward in the direction in which the thin section is discharged by the transport surface, the liquid phase, which is formed between the transport surface and the sample table and is positioned at a side of the transfer advancement direction, is extended in the transfer advancement direction along the inclination of the sample table. Accordingly, the thin section is smoothly transferred onto the sample table.

According to a fifth aspect of the present invention, in the thin-section sample fabrication apparatus of the first aspect, the liquid phase forming portion may include a transfer liquid supply portion that supplies a predetermined amount of transfer liquid onto the sample table, and a proximity displacement mechanism that relatively displaces the sample table and the thin-section transfer portion positioned at a side of the transporting mechanism so that droplets of the transfer liquid on the sample table are connected to the transport surface.

If the predetermined amount of transfer liquid is supplied from the transfer liquid supply portion onto the sample table, droplets having the predetermined amount of transfer liquid are formed on the sample table. If the sample table and the thin-section transfer portion are relatively displaced by the proximity displacement mechanism after the droplets are formed, the droplets of the transfer liquid on the sample table are connected to the transport surface. As a result, the liquid phase continuing from the transport surface onto the sample table is formed.

According to a sixth aspect of the present invention, there is provided a method of fabricating a thin-section sample which places a thin section, which is cut out from an embedding block in which a biological sample is embedded, onto a sample table, the method including: moving the thin section placed on a transport surface to the vicinity of the sample table; forming a liquid phase having a predetermined amount of transfer liquid which continues from the transport surface onto the sample table, in the vicinity of the sample table; and transferring the thin section placed on the transport surface onto the sample table so that a surface of the thin section opposing the transport surface opposes the sample table by surface tension of the formed liquid phase.

Effects of the Invention

According to the aspects of the present invention, the thin section, which is placed on the transport surface and is moved to the thin-section transfer portion, is transferred onto the sample table via the liquid phase having the transfer liquid continuing from the transport surface onto the sample table. Therefore, it is possible to easily and securely place the thin section, which is placed on the transport surface, onto the sample table using a small amount of transfer liquid.

EMBODIMENTS FOR CARRYING OUT THE INVENTION

Hereinafter, each embodiment of the present invention is described with reference to the drawings.

First Embodiment

Hereinafter, a first embodiment shown in FIGS. 1 to 3A and 3B is described.

Figure 1:
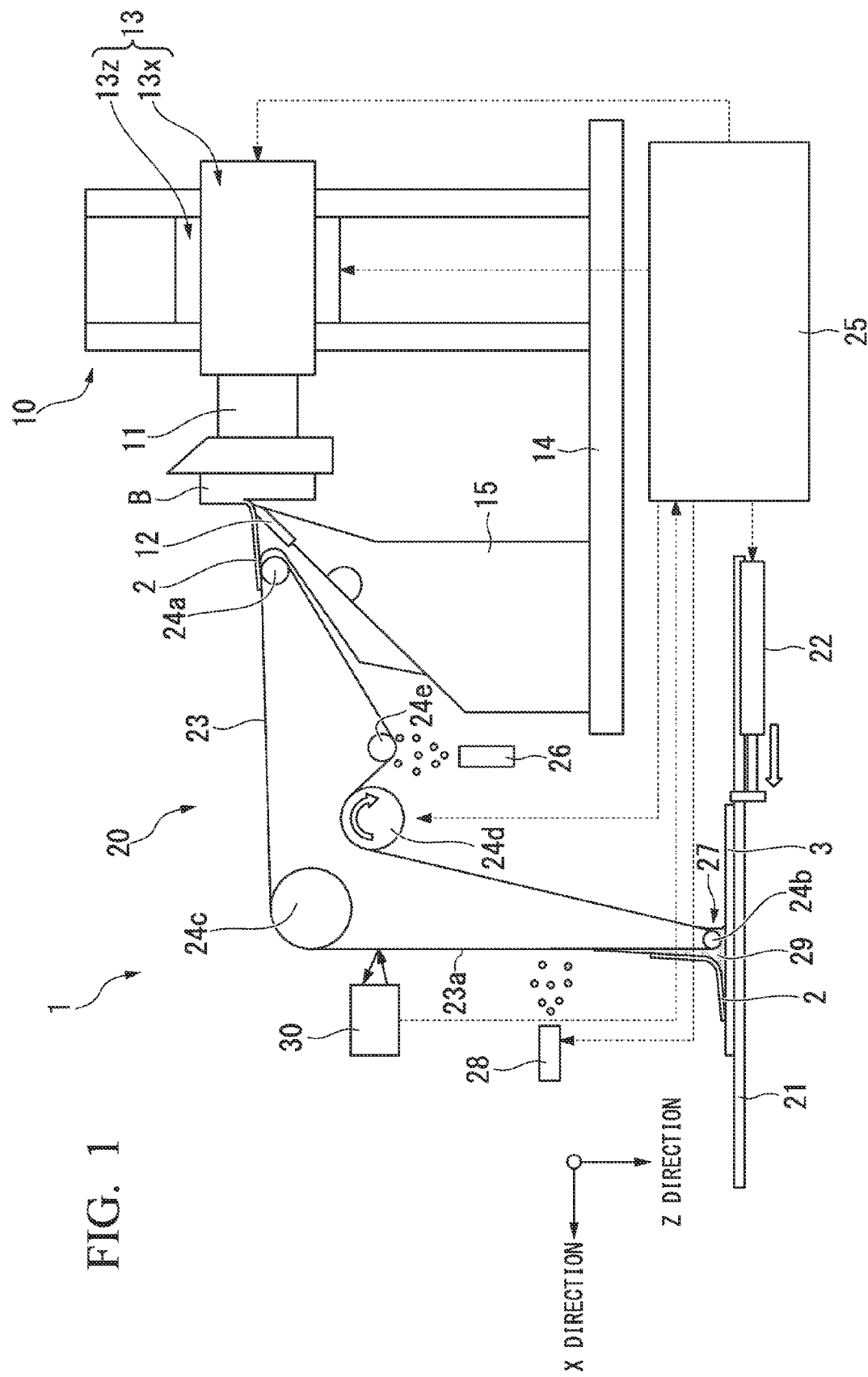
FIG. 1 is a schematic side view showing a schematic structure of a thin-section fabrication apparatus of a first embodiment of the present invention.

FIG. 1 is a view showing a schematic structure of a thin-section sample fabrication apparatus 1 of the present embodiment.

In the thin-section sample fabrication apparatus 1, thin sections 2 fabricated by the thin-section fabrication apparatus 10 are transported to a predetermined position one by one, the transported thin section 2 is placed onto a corresponding slide glass 3 (sample table), and the thin-section sample is fabricated.

The thin-section fabrication apparatus 10 fabricates a very thin section 2 having a thickness of approximately 3 to 5 m from an embedding block B in which a biological sample is embedded. In the embedding block B, the biological sample which is an objected to be observed is embedded by a hydrophobic embedding agent such as paraffin, that is, the outer portion of the biological sample is hardened to be covered, and the embedding block is formed. In the present embodiment, the entire embedding block B is formed in an approximately rectangular parallelepiped shape.

The thin-section fabrication apparatus 10 includes a sample table 11 that fixes the embedding block B, a cutting blade 12 that thinly cuts the embedding block B, and a feed mechanism 13 which is a feed member that moves the sample table 11. In the present embodiment, in the cutting blade 12, a tip portion of a blade edge is fixed to a support block 15 on an installation base 14 so as to face toward obliquely upward (close to sample table 11 or feed mechanisms 13).

The feed mechanism 13 includes a Z stage 13z that moves the sample table 11 forward and backward in a first direction Z (up-down direction in FIG. 1) which is a cutting direction of the cutting blade 12, and an X stage 13x that moves the sample table 11 forward and backward in a second direction X (right-left direction in FIG. 1) which is a thinly sectioned thickness direction of the embedding block B. In the present embodiment, a base portion of the X stage 13x is supported on a movable block of the Z stage 13z. Since a method of operating the sample table forward and backward is a well-known technique, detailed description thereof is omitted. However, for example, power of a motor which is not shown (for example, stepping motor or the like) or an actuator (for example, pneumatic actuator or the like) is transmitted to the Z stage 13z or the X stage 13x via a belt, a rack and pinion, or the like, and the above-described forward and backward operation may be performed.

In a state where the Z stage 13z is raised, the sample table 11 is moved by a cutting thickness in the direction of the cutting blade 12 according to the operation of the X stage 13x. In this state, the Z stage 13z moves downward at a predetermined speed, and the thin section 2 having a predetermined thickness is cut out from an end of a tip of the embedding block B.

The thin-section sample fabrication apparatus 1 includes a transporting mechanism 20 that transports the thin section 2 cut out by the thin-section fabrication apparatus 10, a placement table 21 (installation portion) on which the slide glass 3 which is the sample table is placed, and a forward and backward movement actuator 22 (relative displacement mechanism) that moves the slide glass 3 on the placement table 21 forward and backward in a horizontal direction. The thin sections 2 transported by the transporting mechanism 20 are transferred onto the corresponding slide glass 3 on the placement table 21 one by one. Moreover, the slide glass 3 is formed of a hydrophilic material.

The transporting mechanism 20 includes an annular transport belt 23, and a roller group such as a front folding roller 24a, a rear folding roller 24b, a direction conversion roller 24c, a belt driving roller 24d, or a tension roller 24e over which the transport belt 23 is disposed.

For example, the transport belt 23 may use a member or the like in which hydrophilic processing is performed on a PET film. The transport belt 23 has hydrophilicity, and an outer surface of the transport belt 23 is a transport surface 23a on which the thin section 2 is transported in a state where the thin section 2 is adsorbed by sticking of moisture.

The front folding roller 24a is disposed at a position close to the cutting blade 12 of the thin-section fabrication apparatus 10. The rear folding roller 24b is disposed immediately above a predetermined position on the placement table 21 on which the slide glass 3 is placed. Moreover, the direction conversion roller 24c is disposed at a position which is positioned approximately vertically above the rear folding roller 24b and is positioned to be approximately horizontal to the front folding roller 24a. The belt driving roller 24d and the tension roller 24e are disposed between the front folding roller 24a and the direction conversion roller 24c and at a position below the rollers 24a and 24c. The transport belt 23 is sequentially disposed across the front folding roller 24a, the direction conversion roller 24c, the rear folding roller 24b, the belt driving roller 24d, and the tension roller 24e in this order.

In addition, the transport surface 23a of the transport belt 23 provided across the front folding roller 24a and the direction conversion roller 24c is positioned along the approximately horizontal direction, and the transport surface 23a of the transport belt 23 provided across the direction conversion roller 24c and the rear folding roller 24b is positioned along the approximately vertical direction.

The belt driving roller 24d is driven to be rotated by a motor which is not shown, and the motor is controlled by a controller 25 which is a control portion. Therefore, the transport belt 23 is continuously moved between the roller groups by the control of the controller 25. Moreover, a movement direction of the transport belt 23 by the belt driving roller 24d is a direction in which the transport surface 23a sequentially moves along the front folding roller 24a, the direction conversion roller 24c, and the rear folding roller 24b.

In the lower portion of the tension roller 24e, an adsorption water spray nozzle 26 (adsorption water spray portion) for spraying adsorption water to the transport surface 23a is provided at a position opposing the transport surface 23a (outer circumferential surface) of the transport belt 23. The adsorption water spray nozzle 26 continuously sprays the adsorption water to the transport surface 23a before the direction of the transport belt 23 is changed in the horizontal direction at the front folding roller 24a portion. Accordingly, the thin section 2, which is discharged from the thin-section fabrication apparatus 10 at the front folding roller 24a portion, becomes flat and is adsorbed onto the transport surface 23a.

The portion of the transport belt 23, which is guided by the rear folding roller 24b, is a portion at which the movement direction of the transport surface 23a is continuously changed from the vertical lower portion to the vertical upper portion. In the portion which is continuously changed, a slight gap is maintained between the portion and the upper surface of the slide glass 3 placed on the placement table 21, and a thin-section transfer portion 27 of the transporting mechanism 20, which transfers the thin section 2 onto the slide glass 3, is configured.

In a portion opposing the transport surface 23a between the direction conversion roller 24c and the rear folding roller 24b, a transfer water supply nozzle 28 (transfer liquid supply portion) supplying transfer water, which is water for transferring the thin section 2 from the transport surface 23a onto the slide glass 3, is provided. The transfer water supply nozzle 28 sprays a predetermined amount of transfer water to the transport surface 23a above the slide glass 3, by the control of the controller 25. Accordingly, a liquid phase 29 having the predetermined amount of transfer water is formed to be continuous from the transport surface 23a to the upper surface on the slide glass 3 in the vicinity of the thin-section transfer portion 27. That is, the predetermined amount of transfer water, which is sprayed from the transfer water supply nozzle 28 to the transport surface 23a, flows down along the transport surface 23a and drops on the slide glass 3, and a slight liquid reservoir is formed. A portion of the liquid reservoir is connected to the transport surface 23a of the thin-section transfer portion 27 by a surface tension.

In the present embodiment, the transfer water supply nozzle 28 configures a liquid phase forming portion.

Moreover, in a position opposing the transport surface 23a above the transfer water supply nozzle 28, a thin section detection sensor 30, which detects the thin section 2 adsorbed to the transport surface 23a, is provided. Detection signals of the thin section detection sensor 30 are output to the controller 25, and a control is performed by the controller 25 so that the predetermined amount of transfer water is sprayed from the transfer water supply nozzle 28.

Moreover, the amount (the above-described predetermined amount) of the transfer water supplied from the transfer water supply nozzle 28 to the transport surface 23a is set to an amount in which the transfer water drops from the thin-section transfer portion 27, the liquid reservoir capable of being formed on the slide glass 3 does not overflow from a portion on the slide glass 3, and a portion of the liquid reservoir can be connected to the transport surface of the thin-section transfer portion 27.

Here, the example in which the thin section detection sensor 30 is provided and a passing position of the thin section 2 is detected is described. However, the movement position of the thin section 2 on the transport belt 23 may be calculated from a relationship between a cutting timing by the cutting blade 12 of the thin-section fabrication apparatus 10 and a rotation amount (position) of the belt driving roller 24d. Additionally, the transfer water may be supplied from the transfer water supply nozzle 28 based on the movement position of the calculated thin section 2.

Moreover, the forward and backward movement actuator 22, which moves the slide glass 3 forward and backward on the placement table 21, starts a forward movement at a predetermined timing after the spraying of the transfer water from the transfer water supply nozzle 28 to the transport surface 23a starts. For example, the predetermined timing indicates a timing at which the tip portion (an end at a forward position in the transport direction of the thin section 2) of the transported thin section 2 is transferred to the liquid phase 29 portion, or a timing immediately before the tip portion is transferred to the liquid phase portion. For example, as a calculation method of the timing, information of a time (for example, clock time or the like) at which the transported thin section 2 is detected by the sensor 30 or information of a time at which the thin section passing through a predetermined position is confirmed by a camera (not shown), and information of a time at which the tip of the thin section 2 reaches the liquid phase 29 are calculated according to the rotation amount of the belt driving roller 24d. The information of the calculated time may be the timing. In addition, the tip of the thin section 2 reaching the liquid phase 29 is observed by the camera which is not shown or the like, and the forward movement of the slide glass 3 may start according to the observation state.

The forward and backward movement actuator 22 displaces the slide glass 3 at a predetermined speed in a transfer direction of the thin section 2 by the transport surface 23a. The "transfer direction" of the thin section 2 due to the transport surface 23a means a direction in which an adsorption surface (a surface which is adsorbed to the transport surface 23a heretofore) of the thin section 2 is transferred along the upper surface of the slide glass 3 without being drawn in the changing direction of the transport surface 23a in the vicinity of the thin-section transfer portion 27. Moreover, preferably, a displacement speed (the "predetermined speed") of the slide glass 3 by the forward and backward movement actuator 22 is the same speed as the movement speed of the transport surface 23a, or is a speed which is slightly faster than the movement speed of the transport surface 23a.

Figure 2:
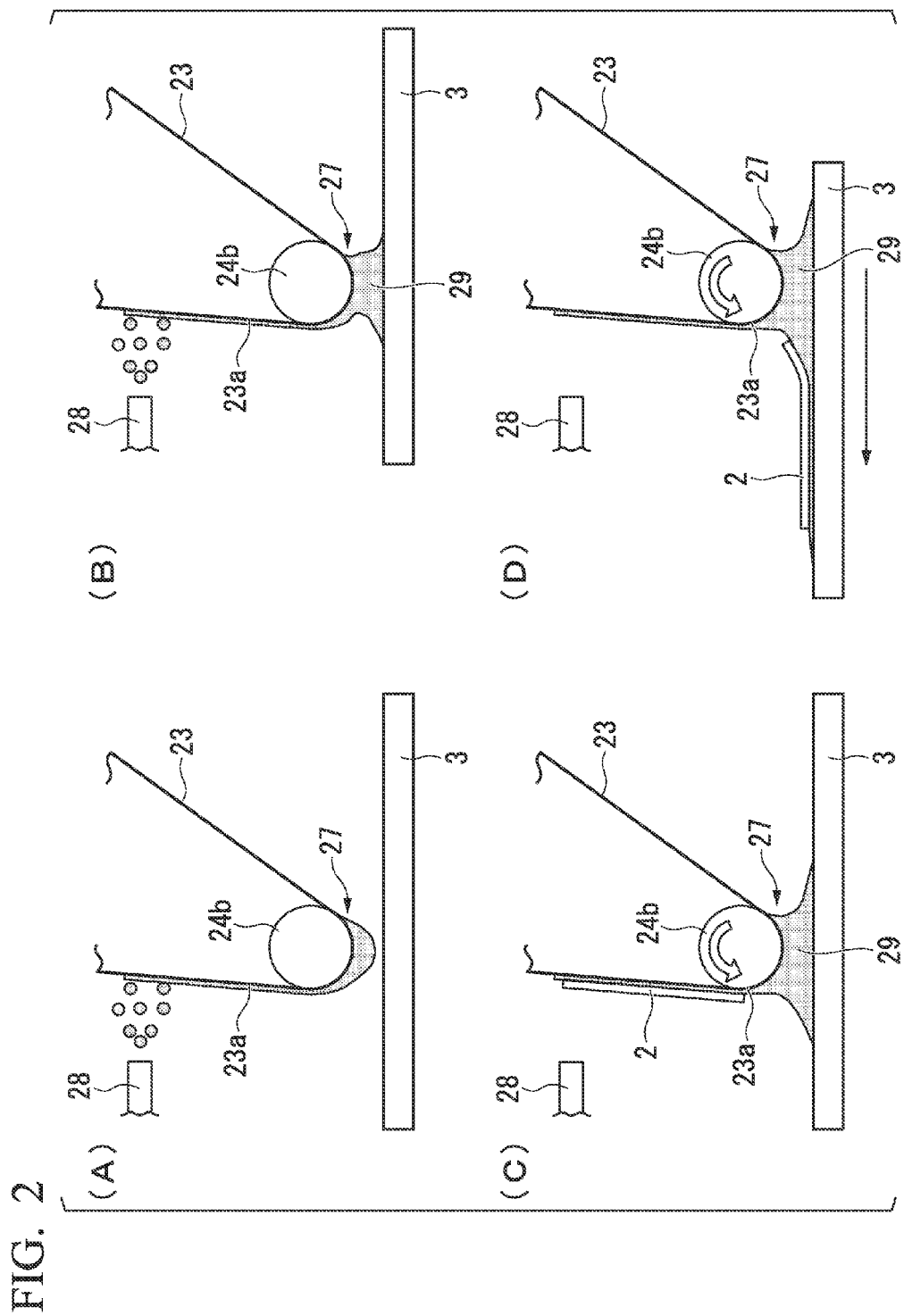
FIG. 2 is a side view sequentially showing changes of a transfer portion of a thin section of the first embodiment of the present invention in order of (A) to (D).

FIG. 2 is a view sequentially showing aspects of the transfer of the thin section 2 from the thin-section transfer portion 27 of the transporting mechanism 20 to the slide glass 3 in order of (A) to (D).

Hereinafter, with reference to FIG. 2 along with FIG. 1, the operation of the thin-section sample fabrication apparatus 1 is described.

If the thin section 2 cut out by the cutting blade 12 of the thin-section fabrication apparatus 10 is sent onto the transport belt 23 in the vicinity of the front folding roller 24a, the thin section 2 is adsorbed onto the transport surface 23a by the surface tension of the water. As a result, the thin section 2 moves toward the rear folding roller 24b portion along with the movement of the transport surface 23a. The cut-out thin section 2 is formed by flat portions and end surface portions which are connected to the flat portions. The flat portion of the thin section 2 adsorbed to the transport surface 23a is referred to as a "surface of the thin section 2 opposing to the transport surface 23a". During the above-described operation, the slide glass 3 is installed at a defined position immediately below the thin-section transfer portion 27 on the placement table 21.

If the thin section 2 passes through the front surface of the thin section detection sensor 30, the detection signal is output from the thin section detection sensor 30 to the controller 25, and a predetermined amount of transfer water is supplied from the transfer water supply nozzle 28 onto the transport surface 23a by the control of the controller 25. As shown in (A) of FIG. 2, the supply of the transfer water is performed above the thin-section transfer portion 27 of the transporting mechanism 20.

If the supply of the transfer water is continued, as shown in (B) and (C) of FIG. 2, the transfer water dropping from the lower end of the transport surface 23a of the thin-section transfer portion 27 forms the liquid reservoir on the slide glass 3, and a portion of the liquid reservoir is connected to the transport surface 23a. If the liquid reservoir is gradually enlarged, a region positioned at which the transport surface 23a of the thin-section transfer portion 27 faces the transfer water supply nozzle 28, and the upper surface of the slide glass 3 are connected to each other by the smooth liquid phase 29 of the transfer water.

At this time, if the thin section 2 on the transport surface 23a reaches a portion of the liquid phase 29, the tip portion of the hydrophobic thin section 2 is smoothly separated from the transport surface 23a, and is transferred to the liquid phase 29 portion from the surface opposing the transport surface 23a of the thin section 2. The forward movement of the forward and backward movement actuator 22 starts at the timing at which the tip portion of the thin section 2 is transferred to the liquid phase 29 portion or at the time immediately before the tip portion is transferred to the liquid phase portion. Therefore, as shown in (D) of FIG. 2, the slide glass 3 is moved forward in the transfer direction (a straight-line arrow direction in the drawing) at the predetermined speed.

As a result, the liquid phase 29 is forcibly enlarged in the transfer direction along with the movement of the slide glass 3, and the thin section 2 is securely transferred to the upper portion of the slide glass 3 along the liquid phase 29.

Moreover, when the movement speed of the slide glass 3 by the forward and backward movement actuator 22 is slightly faster than the movement speed of the transport surface 23a, the thin section 2 is extended, and wrinkles or slack of the thin section 2 can be removed. Moreover, when the movement speed of the slide glass 3 by the forward and backward movement actuator 22 is the same as the movement speed of the transport surface 23a, possibility of tearing of the thin section 2 can be decreased.

Figure 3A:
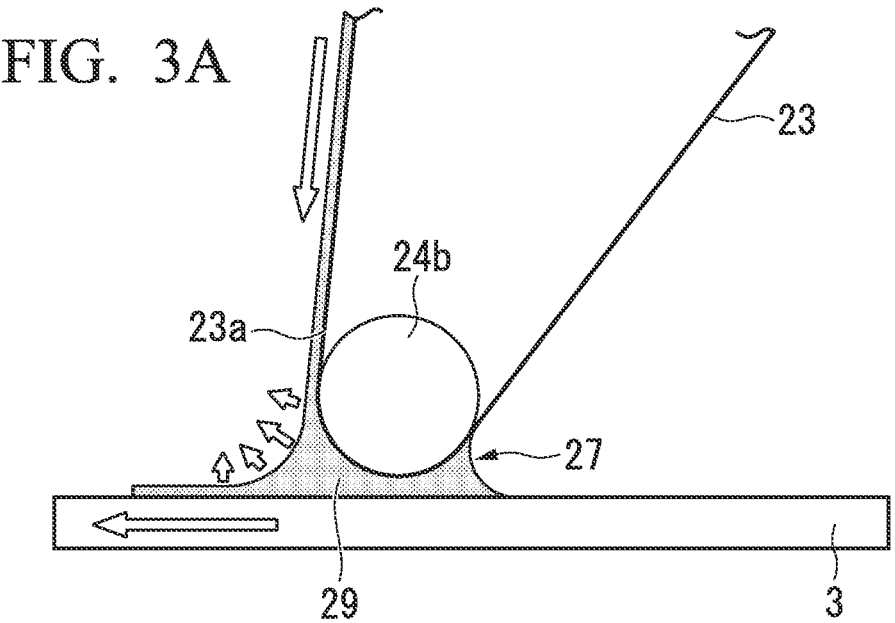
FIG. 3A is a side view of the transfer portion of the thin section of the first embodiment of the present invention.
Figure 3B:
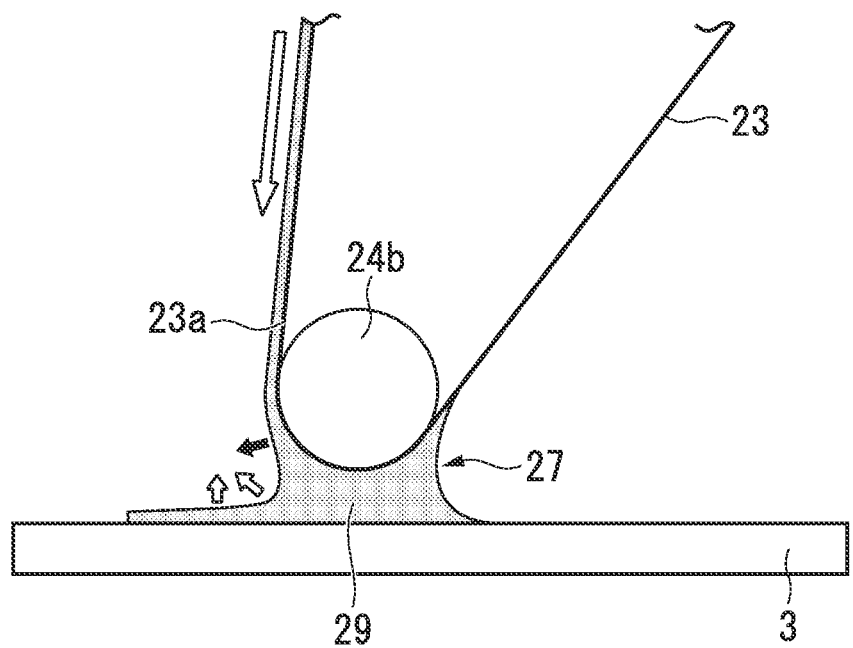
FIG. 3B is a side view of a transfer portion of a thin section of Comparative Example with respect to the transfer portion of the thin section of FIG. 3A.

FIG. 3A is a view showing an aspect of the change of the liquid phase 29 in the transfer direction (transfer advancement direction) when the slide glass 3 moves in the transfer direction due to the forward and backward movement actuator 22, and FIG. 3B is a view showing an aspect of the change of the liquid phase 29 in the transfer direction when the slide glass 3 is not moved.

As shown in FIG. 3A, when the slide glass 3 is moved in the transfer direction, all normal vectors of the surface of the liquid phase 29 in the transfer direction face the upper portion with respect to the upper surface of the slide glass 3. As shown in FIG. 3B, when the slide glass 3 is not moved, there is possibility that a portion of normal vectors of the surface of the liquid phase 29 in the transfer direction may face the lower portion with respect to the upper surface of the slide glass 3. In the lower end of the thin-section transfer portion 27, since the transport surface of the transport belt moves in a direction opposing the appropriate movement direction according to the rotation of the rear folding roller 24b, the liquid phase positioned at a side of the transfer direction is pulled in the opposing direction. Therefore, there is possibility that a portion of the normal vectors may face the lower portion with respect to the upper surface of the slide glass 3.

Therefore, in the case of the present embodiment, since all normal vectors of the surface of the liquid phase 29 in the transfer direction face the upper portion of the slide glass 3, the thin section 2 transferred to the liquid phase 29 portion is not drawn in the direction opposing the transfer direction.

As described above, in the thin-section sample fabrication apparatus 1, a predetermined amount of liquid phase 29 continuous from the transport surface 23a of the lower end of the transport belt 23 to the upper surface of the slide glass 3 is formed by the transfer water supplied from the transfer water supply nozzle 28 to the transport belt 23. Moreover, the thin section 2, which is adsorbed to the transport surface 23a and is moved to the thin-section transfer portion 27, is transferred from the surface opposing the transfer surface 23a of the thin section 2 onto the slide glass 3 via the liquid phase 29 of the transfer water. Accordingly, the thin section 2 adsorbed to the transport surface 23a can be easily and securely placed to the slide glass 3 using a small amount of transfer water.

In addition, in the thin-section sample fabrication apparatus 1, it is not necessary to use a large liquid tank. Accordingly, an absolute amount of the treated water can be largely decreased, the size of the entire apparatus is decreased, and the apparatus can be manufactured at a low cost. In addition, the thin-section sample fabrication apparatus 1 is not an apparatus having a shape in which the slide glass 3 is immersed in a large volume of liquid, and possibility of entering of bubbles due to the thin section 2 can be decreased.

In the thin-section sample fabrication apparatus 1, in the position above the slide glass 3, the transfer water is supplied to the transport surface 23a of the transport belt 23 from the transfer water supply nozzle 28 to form the liquid phase 29. Therefore, just by adjusting the amount and the supply timing of the transfer water supplied from the transfer water supply nozzle 28 to the transport surface 23a, the liquid phase 29 can be easily formed.

In the thin-section sample fabrication apparatus 1 of the present embodiment, when the thin section 2 is transferred from the transport surface 23a onto the slide glass 3 via the liquid phase, the slide glass 3 is displaced in the transfer direction by the forward and backward movement actuator 22 which is the relative displacement mechanism. Therefore, the curved shape of the surface of the liquid phase 29 in the transfer direction (transfer advancement direction) is forcibly extended, and the thin section 2 can be more smoothly transferred onto the slide glass 3. Moreover, by changing the relative movement speed between the thin section 2 and the slide glass 3, the tension applied to the thin section 2 can be easily controlled.

In addition, in the above-described example, the slide glass 3 is moved by the forward and backward movement actuator 22. However, the thin-section transfer portion 27 of the transporting mechanism 20 may be moved in the opposing direction.

Second Embodiment

Figure 4:
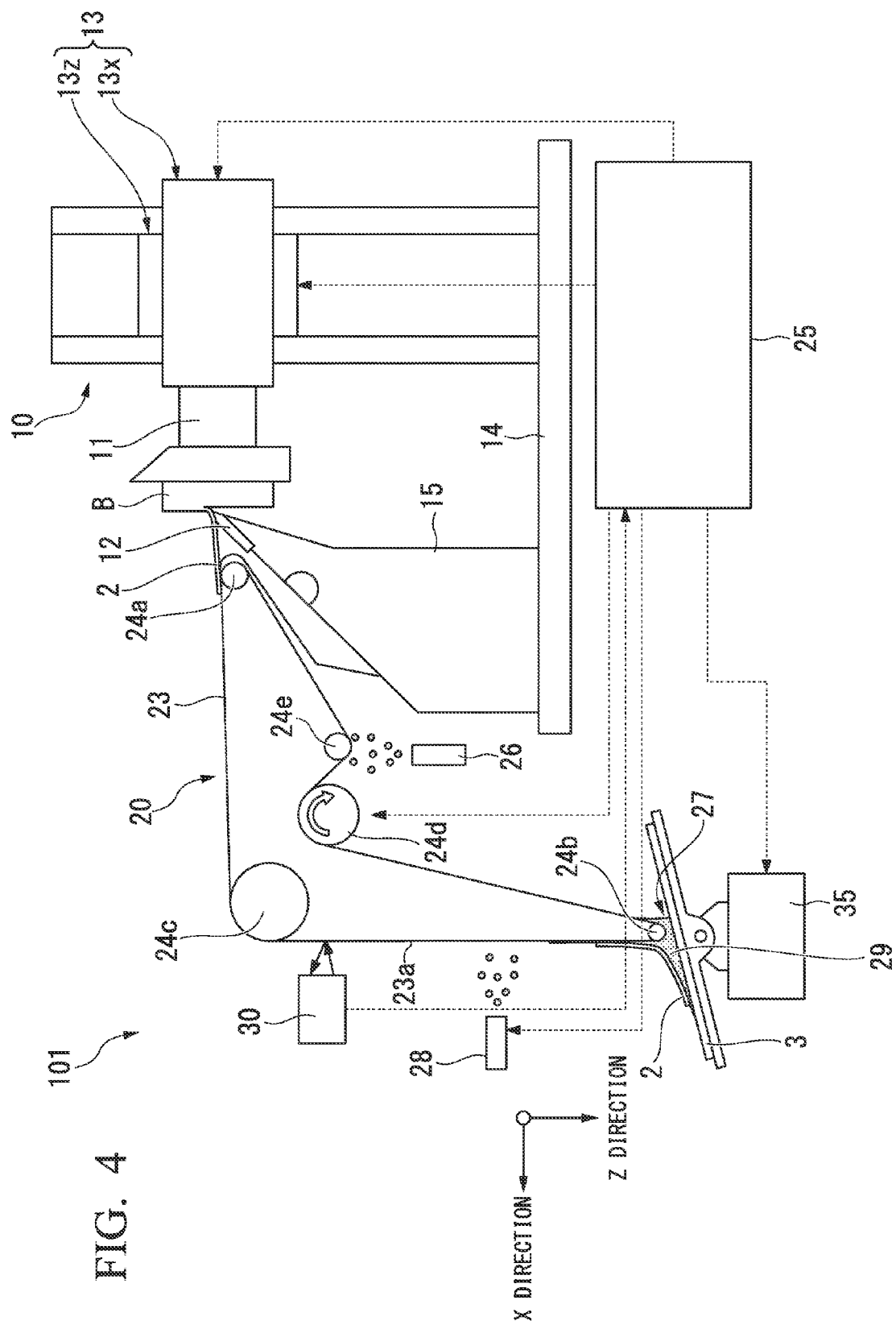
FIG. 4 is a schematic side view showing a schematic structure of a thin-section fabrication apparatus of a second embodiment of the present invention.

Hereinafter, a second embodiment shown in FIG. 4 is described. Moreover, the same reference numerals are assigned to the same portions as the first embodiment and overlapping description is omitted, which is similarly applied to a third embodiment described below.

FIG. 4 is a view showing a schematic structure of a thin-section sample fabrication apparatus 101 of the present embodiment.

The thin-section sample fabrication apparatus 101 of the present embodiment is different from the thin-section sample fabrication apparatus 1 of the first embodiment in that an inclination actuator 35 (sample table inclination mechanism) capable of forming an inclination angle of the slide glass 3 is provided instead of the forward and backward movement actuator 22 of the first embodiment, and other structures are similar to each other.

According to the control of the controller 25, the inclination actuator 35 inclines the slide glass 3 downward in the discharging direction of the thin section 2 by the transport surface 23a at a predetermined timing after the supply of the transfer water from the transfer water supply nozzle 28 to the transport surface 23a starts. For example, as the predetermined timing, a timing of an extent in which the thin section 2 is securely transferred, and a time at which the transfer water drops (that is, the transfer water having an extent, in which the thin section 2 is securely transferred to the upper portion of the slide glass 3 and the liquid phase 29 is formed, drops) on the slide glass 3 can be assumed. For example, according to a test or the like, the transfer water is actually supplied from the transfer water supply nozzle 28 to the transport surface 23a, the amount and the time of the transfer water dropping on the slide glass 3 are measured, and the measured time may be set to the predetermined timing.

In the thin-section sample fabrication apparatus 101 of the present embodiment, after the transfer water drops on the slide glass 3 from the transport surface 23a, the slide glass 3 is inclined downward in the transfer direction of the thin section 2 by the transport surface 23a. Therefore, the transfer water dropping on the slide glass 3 spreads in the transfer direction by gravity, and the thin section 2 is securely transferred to the upper portion of the slide glass 3 along the liquid phase 29. Moreover, the tension applied to the thin section 2 in the transfer process is decreased.

Third Embodiment

Figure 5:
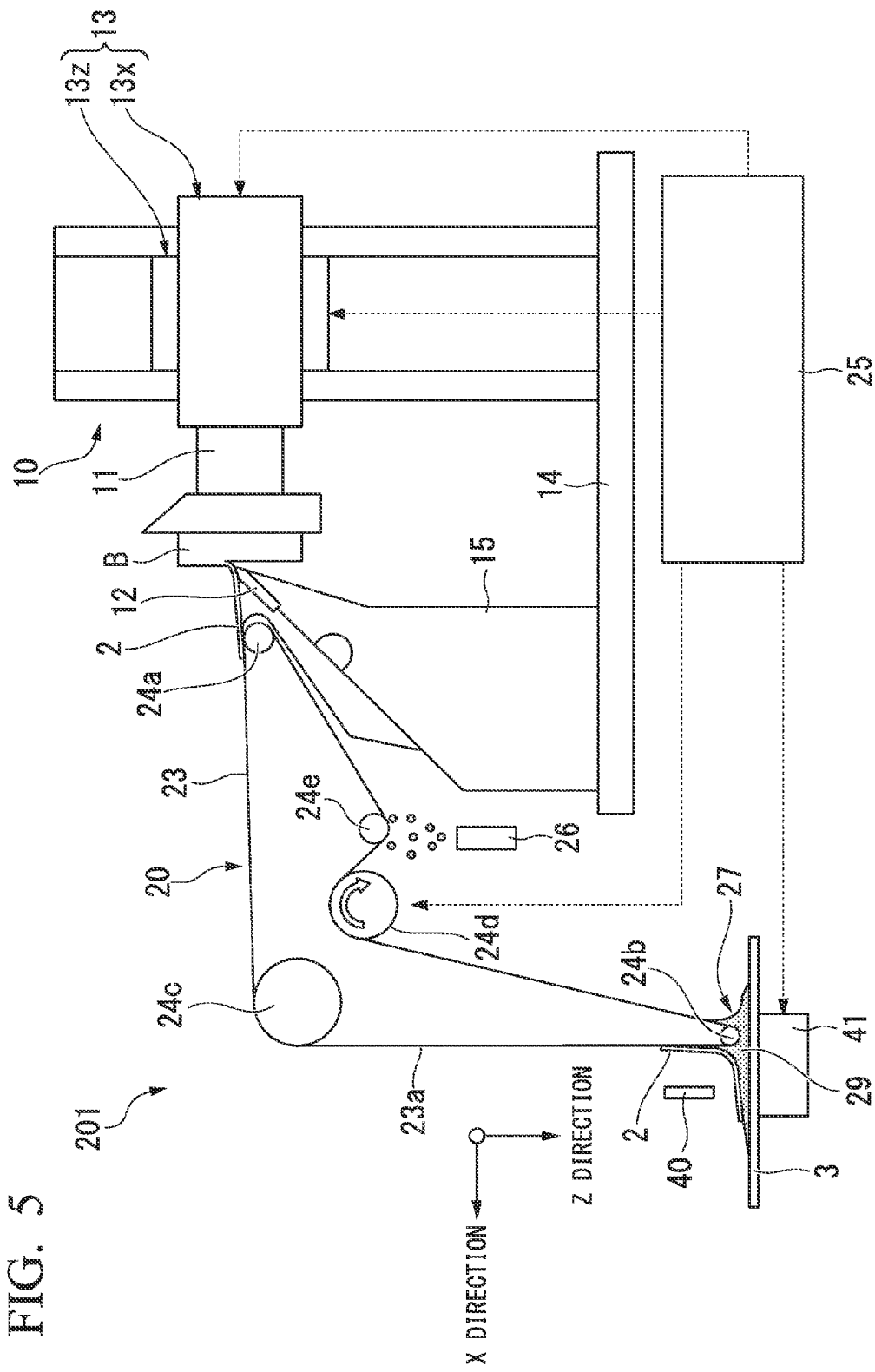
FIG. 5 is a schematic side view showing a schematic structure of a thin-section fabrication apparatus of a third embodiment of the present invention.
Figure 6:
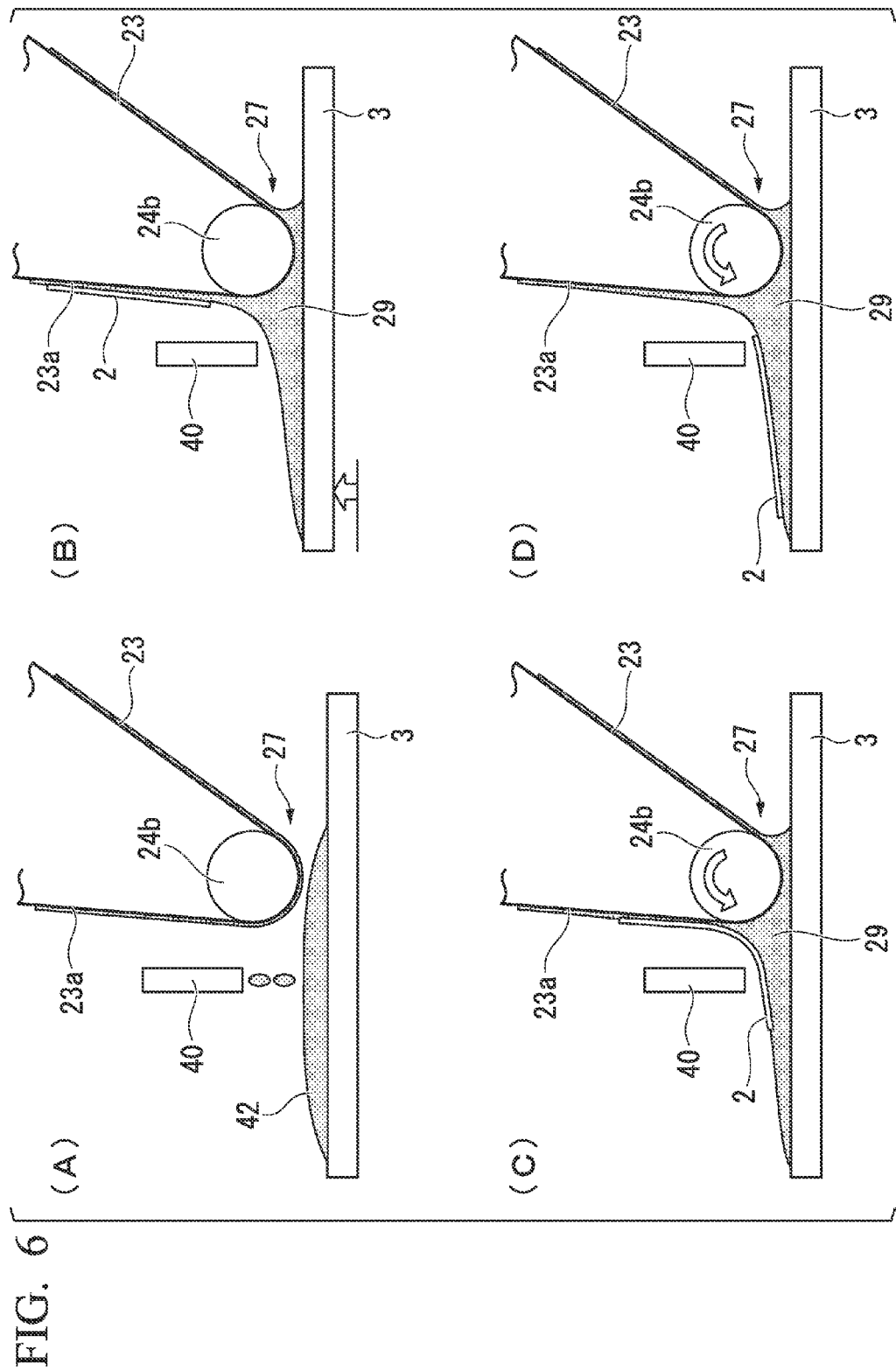
FIG. 6 is a side view sequentially showing changes of a transfer portion of a thin section of the third embodiment of the present invention in order of (A) to (D).

Hereinafter, a third embodiment shown in FIGS. 5 and 6 is described.

FIG. 5 is a view showing a schematic structure of a thin-section sample fabrication apparatus 201 of the present embodiment.

The basic structure of the thin-section sample fabrication apparatus 201 of the present embodiment is substantially the same as that of the thin-section sample fabrication apparatus 1 of the first embodiment. However, the basic structure of the present embodiment is different from that of the first embodiment with respect to the structure of the liquid phase forming portion forming the liquid phase 29.

In the first embodiment, the transfer water supply nozzle 28, which supplies the transfer water to the transport surface 23a of the transport belt 23 to form the liquid phase 29, is provided. However, in the thin-section sample fabrication apparatus 201 of the present embodiment, a transfer water dropping nozzle 40 (transfer liquid supply portion) which directly drops a predetermined amount of transfer water on the slide glass 3 and a lifting and lowering actuator 41 (proximity displacement mechanism) which lifts and lowers the slide glass 3 are provided, and the transfer water dropping nozzle and the lifting and lowering actuator configure the liquid phase forming portion. For example, the lifting and lowering actuator 41 transmits power of a motor which is not shown (for example, stepping motor or the like) or an actuator which is not shown (for example, pneumatic actuator or the like) to the slide glass 3 via a belt, a rack and pinion, or the like, and lifts and lowers the slide glass 3.

FIG. 6 is a view sequentially showing aspects of the transfer of the thin section 2 from the thin-section transfer portion 27 of the transporting mechanism 20 to the slide glass 3 in order of (A) to (D).

As shown in (A) of FIG. 6, the transfer water directly drops on the slide glass 3 from the transfer water dropping nozzle 40. When the transfer water drops, the slide glass 3 is maintained in a state where the glass is largely separated downward from the thin-section transfer portion 27 by the lifting and lowering actuator 41. Accordingly, even when the transfer water drops on the slide glass 3 and droplets 42 gradually spread, the upper portion of the droplet 42 does not contact the transport surface 23a of the thin-section transfer portion 27.

After this, the droplets 42 formed on the slide glass 3 are connected to the transport surface 23a of the thin-section transfer portion 27, and the liquid phase 29 which transfers the thin section 2 onto the slide glass 3 is formed. Therefore, in the transfer direction, at a position anterior to a contact portion (a portion immediately below the rear folding roller 24b) between the droplets and the transport surface 23a, the droplets need to exist in a range which at least corresponds to the length of the thin section 2. Therefore, the transfer water dropping nozzle 40 is installed at a position, at which the droplets 42 having a width corresponding to a sum of a diameter of the rear folding roller 24b in addition to the length of the thin section is formed, in the transfer direction from the end of the rear folding roller 24b.

If the droplets 42 are formed on the slide glass 3 as described above, next, the slide glass 3 is lifted by a predetermined amount by the lifting and lowering actuator 41. Accordingly, as shown in (B) of FIG. 6, the droplets 42 are connected to the transport surface 23a which is positioned at the thin-section transfer portion 27. Therefore, the liquid phase 29, which continues from the transport surface 23a to the upper surface of the slide glass 3, is formed.

If the thin section 2 on the transport surface 23a reaches the liquid phase 29 portion after the liquid phase 29 is formed, as shown in (C) of FIG. 6, the tip portion of the thin section 2 is separated from the transport surface 23a, and the thin section is transferred to the liquid phase 29 portion. At this time, since the liquid phase 29 smoothly continues in the transfer direction of the slide glass 3 from the transport surface 23a, as shown in (D) of FIG. 6, the thin section 2 is easily and securely transferred to the upper portion of the slide glass 3.

In addition, the example, in which the slide glass 3 is lifted by the lifting and lowering actuator 41 to connect the droplets 42 on the slide glass 3 to the transport surface 23a, is described. On the other hand, the thin-section transfer portion 27 of the transporting mechanism 20 may be lowered in the direction of the slide glass 3.

Basically, the thin-section sample fabrication apparatus 201 of the present embodiment can obtain effects approximately similar to the first and second embodiments. Moreover, since the transfer water directly drops on the slide glass 3 from the transfer water dropping nozzle 40, there is an advantage that the amount of the transfer water forming the liquid phase 29 can be correctly managed.

In addition, in a state where the slide glass 3 approaches the transport surface 23a in advance, the amount of the transfer water dropping from the transfer water dropping nozzle 40 is increased, and the droplets 42 can be connected to the transport surface 23a. On the other hand, when the slide glass 3 is separated from the transport surface 23a in advance and the slide glass 3 is moved relative to the thin-section transfer portion 27 by the lifting and lowering actuator 41 or the like, overflowing of the droplets 42 from the slide glass 3 can be prevented.

In addition, the present invention is not limited to the above-described embodiments, and various design changes can be performed within a scope which does not depart from the gist.

INDUSTRIAL APPLICABILITY

The present invention can be applied to a thin-section sample fabrication apparatus which fabricates a thin-section sample used in physics and chemistry experiments, microscope observations, or the like, and a method of fabricating the same.

DESCRIPTION OF THE REFERENCE SYMBOLS 1, 101, and 201: thin-section sample fabrication apparatus
2: thin section
3: slide glass (sample table)
20: transporting mechanism
21: placement table (installation portion)
22: forward and backward movement actuator (relative displacement mechanism)
23a: transport surface
27: thin-section transfer portion
28: transfer water supply nozzle (liquid phase forming portion)
29: liquid phase
35: inclination actuator (sample table inclination mechanism)
40: transfer water dropping nozzle (transfer liquid supply portion)
41: lifting and lowering actuator (proximity displacement mechanism)
B: embedding block

What is claimed is:
1. A thin-section sample fabrication apparatus comprising:

a sample table that places a thin section cut out from an embedding block in which a biological sample is embedded;

a transporting mechanism that comprises a transport surface on which the thin section is placed, and moves the thin section placed on the transport surface to the vicinity of the sample table;

a liquid phase forming portion that forms a liquid phase having a predetermined amount of transfer liquid which continues from the transport surface onto the sample table in the vicinity of the sample table;

a roller that is disposed immediately above a predetermined position on a placement table on which the sample table is placed;

a thin-section transfer portion that maintains a slight gap between a portion of the transport surface that is guided by the roller and an upper surface of the sample table placed on the placement table, and transfers the thin section placed on the transport surface onto the sample table; and a relative displacement mechanism that relatively displaces the sample table and the thin-section transfer portion in a transfer direction of the thin section onto the sample table when the thin section is transferred from the transport surface onto the sample table, wherein the liquid phase forming portion supplies the transfer liquid to the transport surface, and forms the liquid phase having the predetermined amount of transfer liquid continuing from the transport surface onto the sample table.

2. The thin-section sample fabrication apparatus according to claim 1, wherein the portion of the transport surface that is guided by the roller is a portion at which a movement direction of the transport surface is continuously changed from a vertical lower portion to a vertical upper portion.

3. A method of fabricating a thin-section sample which places a thin section, which is cut out from an embedding block in which a biological sample is embedded, onto a sample table, the method comprising:

moving the thin section placed on a transport surface to the vicinity of the sample table;

forming a liquid phase having a predetermined amount of transfer liquid which continues from the transport surface onto the sample table, in the vicinity of the sample table; and transferring the thin section placed on the transport surface onto the sample table so that a surface of the thin section opposing the transport surface opposes the sample table by surface tension of the formed liquid phase.

* * * * *